(12) United States Patent
Raisoni

(10) Patent No.: US 10,966,219 B2
(45) Date of Patent: *Mar. 30, 2021

(54) COMMUNICATION BETWEEN DEVICES USING A WIRELESS COMMUNICATION PROTOCOL

(71) Applicant: Senseonics, Incorporated, Germantown, MD (US)

(72) Inventor: Barkha Raisoni, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/847,112

(22) Filed: Apr. 13, 2020

(65) Prior Publication Data

US 2020/0245342 A1    Jul. 30, 2020

Related U.S. Application Data

(63) Continuation of application No. 15/625,359, filed on Jun. 16, 2017, now Pat. No. 10,624,104.

(Continued)

(51) Int. Cl.
*H04W 72/12* (2009.01)
*H04W 76/10* (2018.01)
*H04W 76/25* (2018.01)

(52) U.S. Cl.
CPC .......... *H04W 72/12* (2013.01); *H04W 76/10* (2018.02); *H04W 76/25* (2018.02)

(58) Field of Classification Search
CPC ...... H04W 72/12; H04W 76/10; H04W 76/25
(Continued)

(56) References Cited

U.S. PATENT DOCUMENTS 6,813,519 B2    11/2004  Lebel et al.
8,484,370 B1     7/2013  Coffee et al.
(Continued)

OTHER PUBLICATIONS

Edorphy; Significant change to connection interval and packets per interval; Jun. 18, 2015; Apple Developer Forums. https://forums.developer.apple.com/thread/6025 (Year: 2015).

*Primary Examiner* — Christopher R Crompton
(74) *Attorney, Agent, or Firm* — Rothwell, Figg, Ernst & Manbeck, P.C.

(57) ABSTRACT

A first communication device may communicate wirelessly with a second communication device. The first communication device may include a wireless communication integrated circuit (IC) configured to (i) receive application data from an application controller, (ii) encapsulate the application data in data packets, and (iii) use an antenna to transmit the data packets. In some embodiments, the first and second communication devices may agree on a length of connection intervals, and the first communication device may transmit two or more of the data packets to the second communication device during each of one or more of the connection intervals. In some embodiments, during periods when there is no application data to encapsulate and transmit to the second communication device, the first communication device may transmit a message to the second communication device, and transmitting the message may keep a wireless link between the first and second communication devices active.

17 Claims, 6 Drawing Sheets

Related U.S. Application Data

(60) Provisional application No. 62/352,369, filed on Jun. 20, 2016.

(58) Field of Classification Search
USPC .................................................. 370/329
See application file for complete search history.

(56) References Cited

U.S. PATENT DOCUMENTS

| | | | |
|---|---|---|---|
| 10,624,104 B2* | 4/2020 | Raisoni | H04W 76/10 |
| 2003/0046991 A1 | 3/2003 | Masson et al. | |
| 2007/0197256 A1 | 8/2007 | Lu et al. | |
| 2008/0214900 A1* | 9/2008 | Fennell | A61B 5/1473 |
| | | | 600/300 |
| 2009/0279464 A1 | 11/2009 | Kakani et al. | |
| 2012/0054752 A1 | 3/2012 | Chin | |
| 2012/0119902 A1 | 5/2012 | Patro et al. | |
| 2013/0007484 A1 | 1/2013 | Gobriel et al. | |
| 2013/0034005 A1 | 2/2013 | Xhafa et al. | |
| 2013/0078912 A1 | 3/2013 | San Vicente et al. | |
| 2013/0159395 A1* | 6/2013 | Backholm | H04L 29/08099 |
| | | | 709/203 |
| 2013/0165181 A1 | 6/2013 | Hasegawa | |
| 2013/0337822 A1 | 12/2013 | Rubin et al. | |
| 2014/0235228 A1 | 8/2014 | Hirako et al. | |
| 2015/0123810 A1 | 5/2015 | Hernandez-Rosas et al. | |
| 2015/0261284 A1 | 9/2015 | Lee et al. | |
| 2016/0173408 A1 | 6/2016 | Lee et al. | |
| 2016/0308748 A1 | 10/2016 | Zuo et al. | |
| 2016/0358361 A1 | 12/2016 | Yang et al. | |
| 2016/0371961 A1* | 12/2016 | Narang | G08B 29/18 |
| 2017/0086136 A1 | 3/2017 | Yu et al. | |
| 2017/0156136 A1 | 6/2017 | Tavildar et al. | |
| 2017/0220401 A1 | 8/2017 | Ren et al. | |
| 2017/0286943 A1 | 10/2017 | Glashan et al. | |
| 2017/0359599 A1 | 12/2017 | He et al. | |
| 2018/0336060 A1 | 11/2018 | Liu et al. | |
| 2019/0021036 A1 | 1/2019 | Shimizu et al. | |
| 2019/0095250 A1 | 3/2019 | Qiang | |
| 2020/0389536 A1* | 12/2020 | Papakostas | H04L 67/325 |

\* cited by examiner

COMMUNICATION BETWEEN DEVICES USING A WIRELESS COMMUNICATION PROTOCOL

CROSS-REFERENCE TO RELATED APPLICATION

This application is a continuation of U.S. application Ser. No. 15/625,359, filed on Jun. 16, 2017, which claims the benefit of priority to U.S. Provisional Application Ser. No. 62/352,369, filed on Jun. 20, 2016, which is incorporated herein by reference in its entirety.

BACKGROUND

Field of Invention

Aspects of the present invention relate to communication between communication devices using a wireless communication protocol. Specifically, aspects of the present invention relate to wireless communication between communication devices of an analyte monitoring system using a wireless communication protocol that restricts packet size, such as the Bluetooth Low Energy (BLE) protocol.

Discussion of the Background

The Bluetooth Low Energy (BLE) protocol enables wireless communication between communication devices (e.g., between a transceiver and a mobile handheld device). BLE is a low energy protocol designed to work with low power applications. BLE permits minimization of radio uptime in exchange for a reduction in data rate. The BLE protocol is significantly different than the standard Bluetooth protocol. Newer communication devices are typically designed to support both the standard Bluetooth protocol as well as the Bluetooth Low Energy protocol. To keep costs down, the same hardware in the communication device typically handles these two protocols.

To keep power consumption low and cost down, the BLE protocol introduces some limitations that do not exist in the standard Bluetooth protocol. For example, in BLE, communication packet sizes are limited to a maximum of 25 octets, and communication speed is limited to 0.3 Mbps. Particular communication devices may impose one or more additional limitations. For example, a particular communication device may limit the communication packet size to a maximum size less than 25 octets. For another example, the operating system (e.g., the iOS mobile operating system) of a mobile handheld device may introduce additional considerations specific to the framework (e.g., an iOS framework such as Core Bluetooth) through which applications access BLE hardware.

Additional considerations specific to the iOS frame may include one or more of the following. First, an iOS device may have access to the BLE hardware only through the Core Bluetooth framework. The iOS device may use a single antenna for both WiFi and Bluetooth (including BLE). In order to limit the opportunity for application writers to seriously affect WiFi performance, Core Bluetooth may limit the minimum connection interval (CI) to a minimum of 18.75 ms. For similar reasons, Core Bluetooth may limit the maximum number of packet pairs per connection interval to 6.

Second, establishing a secure (bonded) connection on the iOS device may be called "Pairing" However, for security reasons, the iOS application may not initiate pairing directly. Instead, to establish a secure BLE connection with the mobile handheld device, the other communication device (a transceiver in an analyte monitoring system) should initiate pairing. If the other communication device is not in the correct state, and the iOS application of the mobile handheld device tries to pair, the communication device with which pairing is attempted may respond with an authentication error. The authentication error may not trigger the iOS device to display a "Pairing" popup dialog, and the user may be prevented from pairing. From the iOS application point of view, this process is transparent.

When operating in background mode, a BLE device may conserve the channels allocated to BLE and, upon observing no communication/data flow over certain period of time, drop the connection. Accordingly, it may be difficult to maintain a connection in case where information is only provided on need basis and not streamed. This is a characteristic for BLE but is not a constraint on the standard Bluetooth. When operating in background mode, an iOS application does not receive discovery notifications for peripherals that have been previously seen. This means that while operating in the background, it is not possible to see the contents of advertising packets as they change, so it is not possible to operate in a mostly-unconnected mode, only connecting when there is data to retrieve.

The iOS application can watch for and re-connect with a known peripheral. If the iOS application subsequently enters the background, it will still receive the usual callbacks if Core Bluetooth sees matching advertisement packets. When operating in the background, the iOS application can freely exchange information with peripherals to which they are connected. The iOS application has approximately 12 seconds to process any incoming packet on the open connection.

There is presently a need in the art for improved wireless communication between communication devices using a wireless communication protocol, such as the BLE protocol, that restricts packet size.

SUMMARY

Aspects of the present invention overcome the disadvantages of prior communication systems by providing, among other advantages, improved wireless communication between communication devices using a wireless communication protocol that restricts packet size. Aspects of the present invention additionally or alternatively provide, among other advantages, improved wireless communication between communication devices in which a wireless communication link between the communication devices is kept active.

One aspect of the invention may provide a first communication device for communicating wirelessly with a second communication device during connection intervals having a length agreed upon by the first and second communication devices. The first communication device may include an application controller, an antenna, and a wireless communication integrated circuit (IC). The application controller may be configured to generate application data. The wireless communication IC may be configured to (i) receive the application data from the application controller, (ii) encapsulate the application data in data packets, and (iii) use the antenna to transmit two or more of the data packets to the second communication device during each of one or more of the connection intervals.

Another aspect of the invention may provide a method for wireless communication between first and second communication devices during connection intervals having a length agreed upon by the first and second communication devices. The method may include using the first communication device to generate application data. The method may include using the first communication device to encapsulate the application data in data packets. The method may include using an antenna of the first communication device to transmit two or more of the data packets during each of one or more of the connection intervals.

Still another aspect of the invention may provide a first communication device for communicating wirelessly with a second communication device over a wireless link between the first and second communication devices. The first communication device may include an application controller, an antenna, and a wireless communication IC. The application controller may be configured to generate application data. The wireless communication IC may be configured to (i) receive application data from the application controller, (ii) encapsulate the received application data in data packets, (iii) use the antenna to transmit the data packets, and (iv) during periods when there is no application data to encapsulate and transmit to the second communication device, use the antenna to transmit a message to the second communication device. Transmitting the message may keep the wireless link between the first and second communication devices active.

Yet another aspect of the invention may provide a method for wireless communication between first and second communication devices over a wireless link between the first and second communication devices. The method may include using the first communication device to generate application data. The method may include using the first communication device to encapsulate the application data in data packets. The method may include using an antenna of the first communication device to transmit the data packets to the second communication device. The method may include, during periods when there is no application data to encapsulate and transmit to the second communication device, using the antenna of the first communication device to transmit a message to the second communication device. Transmitting the message may keep the wireless link between the first and second communication devices active.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION OF PREFERRED EMBODIMENTS

Figure 1:
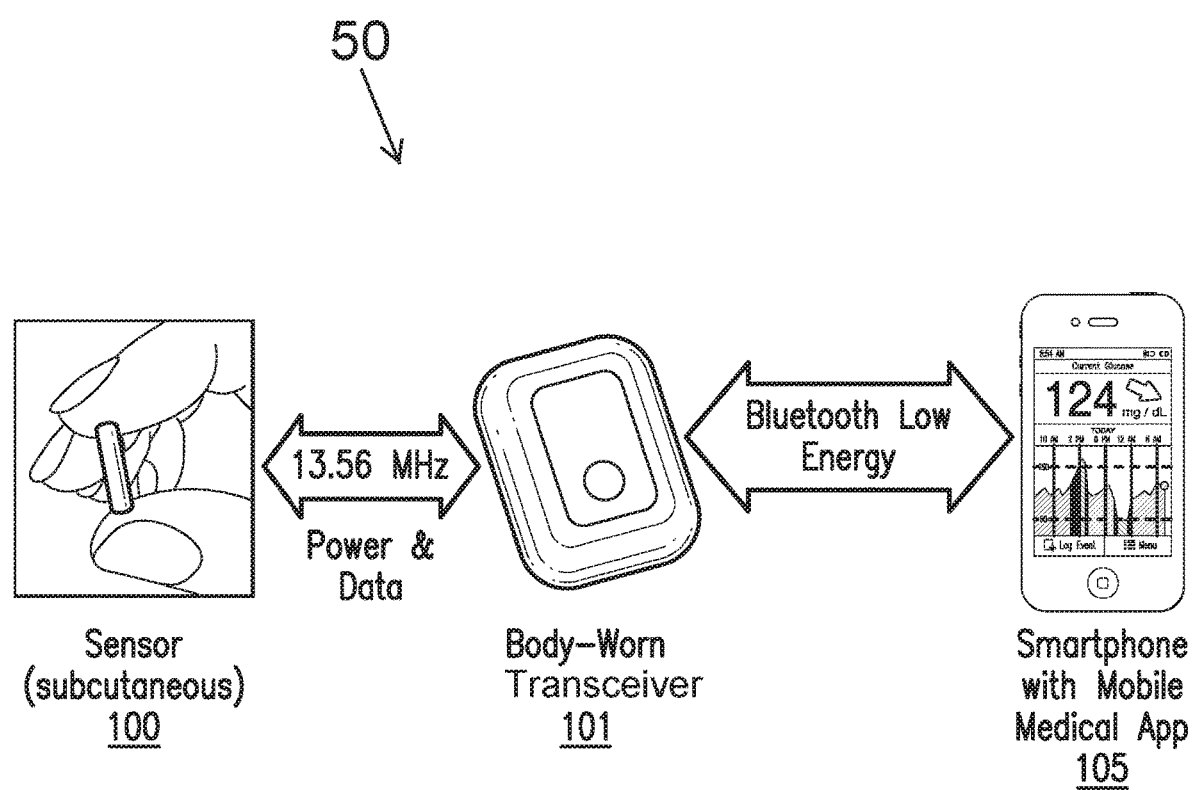
FIG. 1 is a schematic view illustrating an analyte monitoring system embodying aspects of the present invention.

FIG. 1 is a schematic view of an exemplary communication system 50 embodying aspects of the present invention. In some embodiments, the communication system 50 may include one or more of communication devices 100, 101, and 105. In some non-limiting embodiments, the communication system 50 may be an analyte monitoring system. In some non-limiting embodiments, the communication system 50 may be a continuous analyte monitoring system (e.g., a continuous glucose monitoring system). In some non-limiting embodiments where the communication system 50 is an analyte monitoring system, the communication device 100 may be a sensor, the communication device 101 may be a transceiver, and the communication device 105 may be a display device 105. Although the invention is applicable to wireless communication between many different communication devices in many different communication systems, aspects of the invention are described below with reference to non-limiting embodiments in which the communication system 50 is an analyte monitoring system, and the communication devices 100, 101, and 105 are referred to below as a sensor, transceiver, and display device, respectively.

In some embodiments, the sensor 100 may be small, fully subcutaneously implantable sensor measures analyte (e.g., glucose) concentrations in a medium (e.g., interstitial fluid) of a living animal (e.g., a living human). However, this is not required, and, in some alternative embodiments, the sensor 100 may be a partially implantable (e.g., transcutaneous) sensor or a fully external sensor. In some embodiments, the transceiver 101 may be an externally worn transceiver (e.g., attached via an armband, wristband, waistband, or adhesive patch). In some embodiments, the transceiver 101 may remotely power and/or communicate with the sensor to initiate and receive the measurements (e.g., via near field communication (NFC)). However, this is not required, and, in some alternative embodiments, the transceiver 101 may power and/or communicate with the sensor 100 via one or more wired connections. In some non-limiting embodiments, the transceiver 101 may be a smartphone (e.g., an NFC-enabled smartphone) or smartwatch. In some embodiments, the transceiver 101 may communicate information (e.g., one or more analyte concentrations) wirelessly (e.g., via a Bluetooth™ communication standard such as, for example and without limitation Bluetooth Low Energy) to a hand held application running on a display device 105 (e.g., smartphone or smartwatch). In some embodiments, information can be downloaded from the transceiver 101 through a Universal Serial Bus (USB) port. In some embodiments, the communication system 50 may include a web interface for plotting and sharing of uploaded data.

Figure 3:
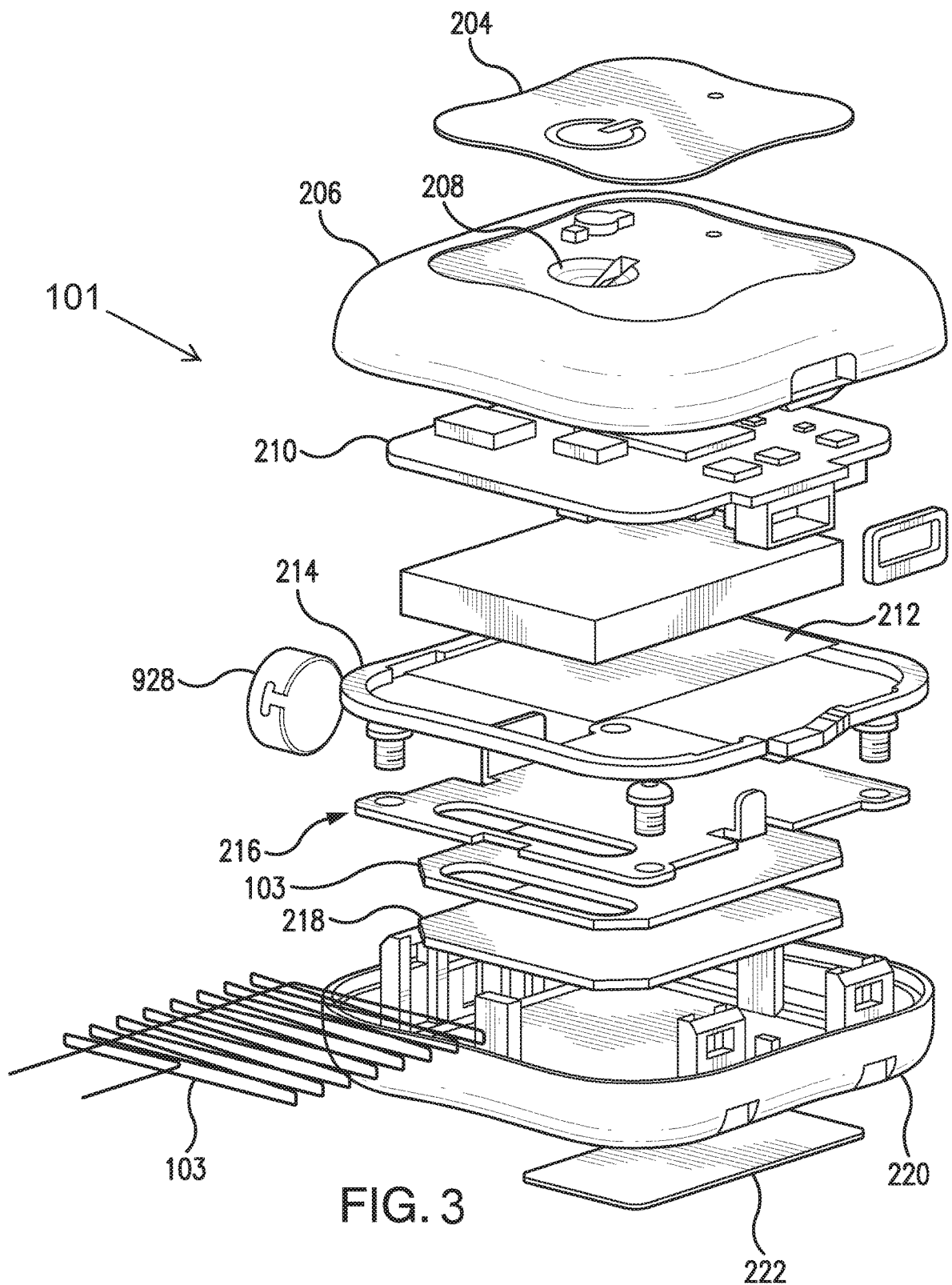
FIG. 3 is an exploded, perspective view of a transceiver embodying aspects of the invention.

In some embodiments, as illustrated in FIG. 3, the transceiver 101 may include an inductive element 103, such as, for example, a coil. The transceiver 101 may generate an electromagnetic wave or electrodynamic field (e.g., by using a coil) to induce a current in an inductive element of the sensor 100, which may power the sensor 100. The transceiver 101 may additionally or alternatively convey data (e.g., commands) to the sensor 100. For example, in a non-limiting embodiment, the transceiver 101 may convey data by modulating the electromagnetic wave used to power the sensor 100 (e.g., by modulating the current flowing through a coil 103 of the transceiver 101). The modulation in the electromagnetic wave generated by the transceiver 101 may be detected/extracted by the sensor 100. Moreover, the transceiver 101 may receive data (e.g., measurement information) from the sensor 100. For example, in a non-limiting embodiment, the transceiver 101 may receive data by detecting modulations in the electromagnetic wave generated by the sensor 100, e.g., by detecting modulations in the current flowing through the coil 103 of the transceiver 101.

The inductive element 103 of the transceiver 101 and the inductive element of the sensor 100 may be in any configuration that permits adequate field strength to be achieved when the two inductive elements are brought within adequate physical proximity.

In some non-limiting embodiments, the sensor 100 may include an analyte indicator element that that exhibits one or more detectable properties (e.g., optical, chemical, or electrical properties) based on the amount or concentration of the analyte in proximity to the analyte indicator element. In some non-limiting embodiments, the sensor 100 may include a temperature transducer. In some embodiments, the sensor 100 may include one or more of the features described in one or more of U.S. application Ser. No. 13/761,839, filed on Feb. 7, 2013, U.S. application Ser. No. 13/937,871, filed on Jul. 9, 2013, and U.S. application Ser. No. 13/650,016, filed on Oct. 11, 2012, all of which are incorporated by reference in their entireties.

Although in some embodiments, the sensor 100 may be an optical sensor, this is not required, and, in one or more alternative embodiments, sensor 100 may be a different type of analyte sensor, such as, for example, an electrochemical sensor, a diffusion sensor, or a pressure sensor. Also, although in some embodiments, the analyte sensor 100 may be a fully implantable sensor, this is not required, and, in some alternative embodiments, the sensor 100 may be a transcutaneous sensor having a wired connection to the transceiver 101. For example, in some alternative embodiments, the sensor 100 may be located in or on a transcutaneous needle (e.g., at the tip thereof). In these embodiments, instead of wirelessly communicating using inductive elements, the sensor 100 and transceiver 101 may communicate using one or more wires connected between the transceiver 101 and the transceiver transcutaneous needle that includes the sensor 100. For another example, in some alternative embodiments, the sensor 100 may be located in a catheter (e.g., for intravenous blood glucose monitoring) and may communicate (wirelessly or using wires) with the transceiver 101.

Figure 2:
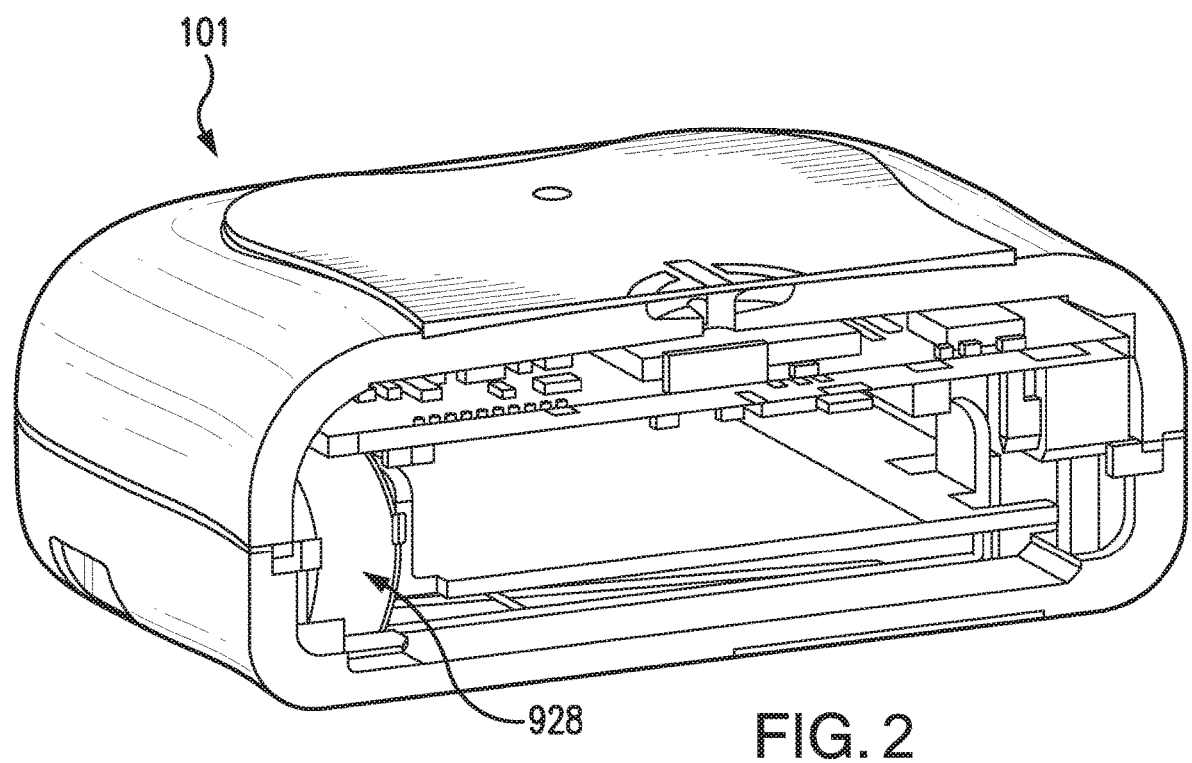
FIG. 2 is cross-sectional, perspective view of a transceiver embodying aspects of the invention.

FIGS. 2 and 3 are cross-sectional and exploded views, respectively, of a non-limiting embodiment of the transceiver 101, which may be included in the communication system 50 illustrated in FIG. 1. As illustrated in FIG. 3, in some non-limiting embodiments, the transceiver 101 may include one or more of a graphic overlay 204, front housing 206, button 208, printed circuit board (PCB) assembly 210, battery 212, gaskets 214, antenna 103, frame 218, reflection plate 216, back housing 220, ID label 222, and/or vibration motor 928. In some non-limiting embodiments, the vibration motor 928 may be attached to the front housing 206 or back housing 220 such that the battery 212 does not dampen the vibration of vibration motor 928. In a non-limiting embodiment, the transceiver electronics may be assembled using standard surface mount device (SMD) reflow and solder techniques. In one embodiment, the electronics and peripherals may be put into a snap together housing design in which the front housing 206 and back housing 220 may be snapped together. In some embodiments, the full assembly process may be performed at a single external electronics house. However, this is not required, and, in alternative embodiments, the transceiver assembly process may be performed at one or more electronics houses, which may be internal, external, or a combination thereof. In some embodiments, the assembled transceiver 101 may be programmed and functionally tested. In some embodiments, assembled transceivers 101 may be packaged into their final shipping containers and be ready for sale.

In some embodiments, as illustrated in FIGS. 2 and 3, the antenna 103 may be contained within the housing 206 and 220 of the transceiver 101. In some embodiments, the antenna 103 in the transceiver 101 may be small and/or flat so that the antenna 103 fits within the housing 206 and 220 of a small, lightweight transceiver 101. In some embodiments, the antenna 103 may be robust and capable of resisting various impacts. In some embodiments, the transceiver 101 may be suitable for placement, for example, on an abdomen area, upper-arm, wrist, or thigh of a patient body. In some non-limiting embodiments, the transceiver 101 may be suitable for attachment to a patient body by means of a biocompatible patch. Although, in some embodiments, the antenna 103 may be contained within the housing 206 and 220 of the transceiver 101, this is not required, and, in some alternative embodiments, a portion or all of the antenna 103 may be located external to the transceiver housing. For example, in some alternative embodiments, antenna 103 may wrap around a user's wrist, arm, leg, or waist such as, for example, the antenna described in U.S. Pat. No. 8,073,548, which is incorporated herein by reference in its entirety.

Figure 4:
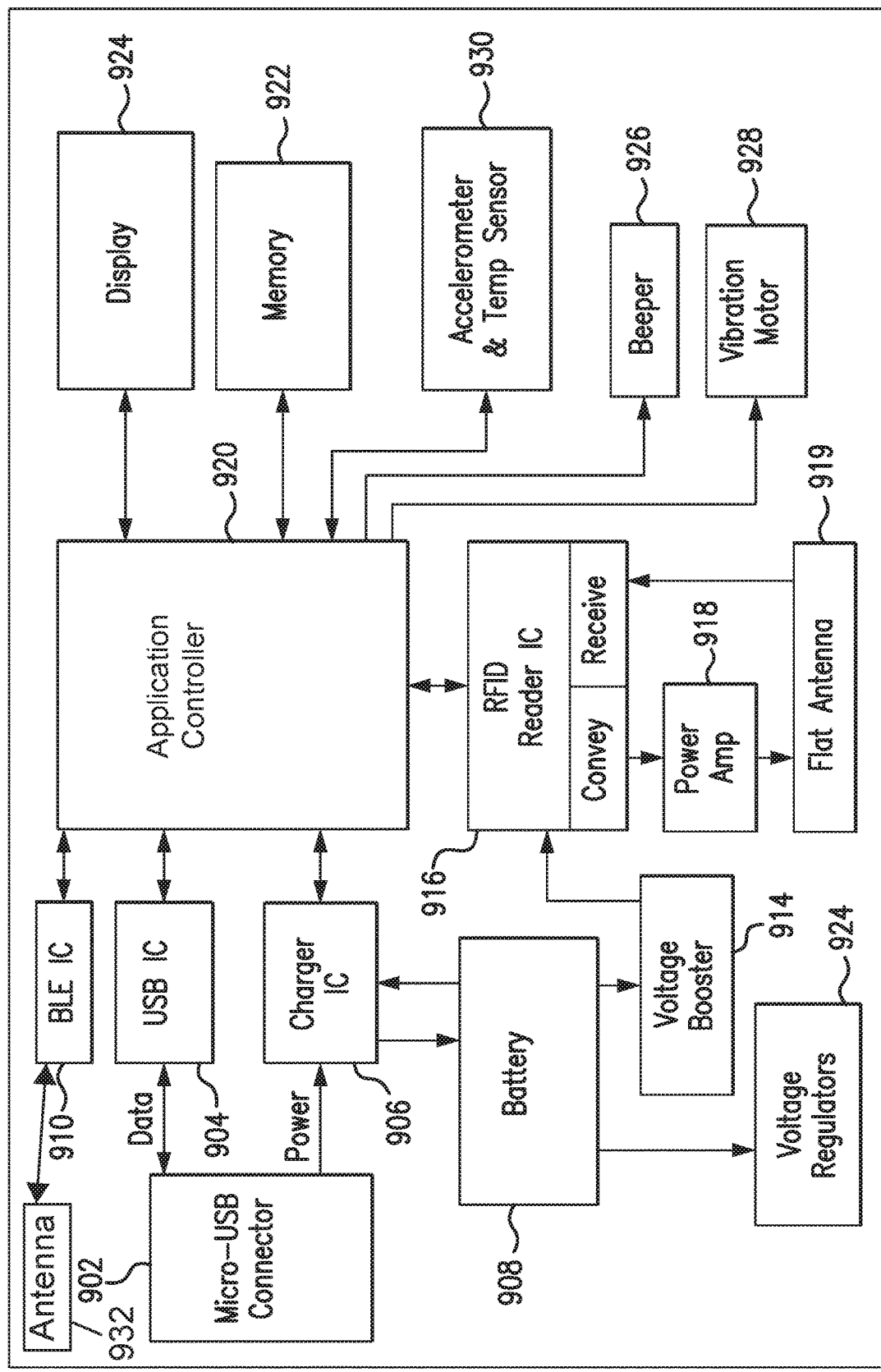
FIG. 4 is a schematic view illustrating a transceiver embodying aspects of the present invention.

FIG. 4 is a schematic view of an external transceiver 101 according to a non-limiting embodiment. In some embodiments, the transceiver 101 may have a connector 902, such as, for example, a Micro-Universal Serial Bus (USB) connector. The connector 902 may enable a wired connection to an external device, such as a personal computer or a display device 105 (e.g., a smartphone or smartwatch).

The transceiver 101 may exchange data to and from the external device through the connector 902 and/or may receive power through the connector 902. The transceiver 101 may include a connector integrated circuit (IC) 904, such as, for example, a USB-IC, which may control transmission and receipt of data through the connector 902. The transceiver 101 may also include a charger IC 906, which may receive power via the connector 902 and charge a battery 908 (e.g., lithium-polymer battery). In some embodiments, the battery 908 may be rechargeable, may have a short recharge duration, and/or may have a small size.

In some embodiments, the transceiver 101 may include one or more connectors in addition to (or as an alternative to) Micro-USB connector 904. For example, in one alternative embodiment, the transceiver 101 may include a spring-based connector (e.g., Pogo pin connector) in addition to (or as an alternative to) Micro-USB connector 904, and the transceiver 101 may use a connection established via the spring-based connector for wired communication to a personal computer or a display device 105 (e.g., a smartphone or smartwatch) and/or to receive power, which may be used, for example, to charge the battery 908.

In some embodiments, the transceiver 101 may have a wireless communication IC 910, which enables wireless communication with an external device, such as, for example, one or more personal computers or one or more display devices 105 (e.g., a smartphone or smartwatch). In some embodiments, the wireless communication IC 910 may include an antenna 932 (e.g., a Bluetooth antenna). In one non-limiting embodiment, the wireless communication IC 910 may employ one or more wireless communication standards to wirelessly transmit and/or receive data via the antenna 932. The wireless communication standard employed may be any suitable wireless communication standard, such as an ANT standard, a Bluetooth standard, or a Bluetooth Low Energy (BLE) standard (e.g., BLE 4.0). In some non-limiting embodiments, the wireless communication IC 910 may be configured to wirelessly transmit and/or receive data at a frequency greater than 1 gigahertz (e.g., 2.4 or 5 GHz). In some non-limiting embodiments, the antenna of the wireless communication IC 910 may be entirely contained within the housing (e.g., housing 206 and 220) of the transceiver 101. However, this is not required, and, in alternative embodiments, all or a portion of the antenna of the wireless communication IC 910 may be external to the transceiver housing.

In some embodiments, the transceiver 101 may include a display interface device, which may enable communication by the transceiver 101 with one or more display devices 105. In some embodiments, the display interface device may include the antenna of the wireless communication IC 910 and/or the connector 902. In some non-limiting embodiments, the display interface device may additionally include the wireless communication IC 910 and/or the connector IC 904.

In some embodiments, the transceiver 101 may include voltage regulators 912 and/or a voltage booster 914. The battery 908 may supply power (via voltage booster 914) to radio-frequency identification (RFID) reader IC 916, which uses the inductive element 103 to convey information (e.g., commands) to the sensor 101 and receive information (e.g., measurement information) from the sensor 100. In some non-limiting embodiments, the sensor 100 and transceiver 101 may communicate using near field communication (NFC) (e.g., at a frequency of 13.56 MHz). In the illustrated embodiment, the inductive element 103 is a flat antenna. In some non-limiting embodiments, the antenna may be flexible. However, as noted above, the inductive element 103 of the transceiver 101 may be in any configuration that permits adequate field strength to be achieved when brought within adequate physical proximity to an inductive element of the sensor 100. In some embodiments, the transceiver 101 may include a power amplifier 918 to amplify the signal to be conveyed by the inductive element 103 to the sensor 100.

The transceiver 101 may include an application controller 920 and a memory 920. The application controller may be, for example and without limitation, a peripheral interface controller (PIC) microcontroller. In some embodiments, the memory 922 may be non-volatile and/or capable of being electronically erased and/or rewritten. The memory 922 may be, for example and without limitation, a Flash memory. In some embodiments, the application controller 920 may control the overall operation of the transceiver 101. For example, the application controller 920 may control the connector IC 904 or wireless communication IC 910 to transmit data via wired or wireless communication and/or control the RFID reader IC 916 to convey data via the inductive element 103. In some embodiments, the application controller 920 may control processing of data received via the inductive element 103, connector 902, or wireless communication IC 910.

In some embodiments, the transceiver 101 may include a sensor interface device, which may enable communication by the transceiver 101 with a sensor 100. In some embodiments, the sensor interface device may include the inductive element 103. In some non-limiting embodiments, the sensor interface device may additionally include the RFID reader IC 916 and/or the power amplifier 918. However, in some alternative embodiments where there exists a wired connection between the sensor 100 and the transceiver 101 (e.g., transcutaneous embodiments), the sensor interface device may include the wired connection.

In some embodiments, the transceiver 101 may include a display 924 (e.g., liquid crystal display and/or one or more light emitting diodes), which application controller 920 may control to display data (e.g., analyte concentration values). In some embodiments, the transceiver 101 may include a speaker 926 (e.g., a beeper) and/or vibration motor 928, which may be activated, for example, in the event that an alarm condition (e.g., detection of a hypoglycemic or hyperglycemic condition) is met. The transceiver 101 may also include one or more additional sensors 930, which may include an accelerometer and/or temperature sensor, that may be used in the processing performed by the application controller 920.

In some embodiments, the transceiver 101 may be a body-worn transceiver that is a rechargeable, external device worn over the sensor implantation or insertion site. The transceiver 101 may supply power to the proximate sensor 100, calculate analyte concentrations from data received from the sensor 100, and/or transmit the calculated analyte concentrations to a display device 105 (see FIG. 1). Power may be supplied to the sensor 100 through an inductive link (e.g., an inductive link of 13.56 MHz). In some embodiments, the transceiver 101 may be placed using an adhesive patch or a specially designed strap or belt. The external transceiver 101 may read measured analyte data from a subcutaneous sensor 100 (e.g., up to a depth of 2 cm or more). The transceiver 101 may periodically (e.g., every 2, 5, or 10 minutes) read sensor data and calculate an analyte concentration and an analyte concentration trend. From this information, the transceiver 101 may also determine if an alert and/or alarm condition exists, which may be signaled to the user (e.g., through vibration by vibration motor 928 and/or an LED of the transceiver's display 924 and/or a display of a display device 105). The information from the transceiver 101 (e.g., calculated analyte concentrations, calculated analyte concentration trends, alerts, alarms, and/or notifications) may be transmitted to a display device 105 (e.g., via Bluetooth Low Energy with Advanced Encryption Standard (AES)-Counter CBC-MAC (CCM) encryption) for display by a mobile medical application (MMA) being executed by the display device 105. In some non-limiting embodiments, the MMA may provide alarms, alerts, and/or notifications in addition to any alerts, alarms, and/or notifications received from the transceiver 101. In one embodiment, the MMA may be configured to provide push notifications. In some embodiments, the transceiver 101 may have a power button (e.g., button 208) to allow the user to turn the device on or off, reset the device, or check the remaining battery life. In some embodiments, the transceiver 101 may have a button, which may be the same button as a power button or an additional button, to suppress one or more user notification signals (e.g., vibration, visual, and/or audible) of the transceiver 101 generated by the transceiver 101 in response to detection of an alert or alarm condition.

In some embodiments, the transceiver 101 of the communication system 50 receives raw signals indicative of an amount or concentration of an analyte in proximity to the analyte indicator element 106 of the analyte sensor 100. In some embodiments, the transceiver 101 may receive the raw signals from the sensor 100 periodically (e.g., every 5, 10, or 20 minutes). In some embodiments, the raw signals may include one or more analyte measurements and/or one or more temperature measurements. In some embodiments, the transceiver 101 may use the received raw signals to calculate analyte concentration. In some embodiments, the transceiver 100 may store one or more calculated analyte concentrations (e.g., in memory 922). In some embodiments, the transceiver 100 may convey one or more calculated analyte concentrations to the display device 105.

In some embodiments, as noted above, the transceiver 101 may utilize a wireless communication protocol for wireless communications to one or more display devices 105, which may be, for example and without limitation, one or more mobile handheld devices (e.g., one or more smartphones). The wireless communication protocol may be, for example and without limitation, Bluetooth Low Energy (BLE). In some embodiments, the transceiver 101 may receive the data from the sensor 100 and calculate an analyte concentration. In some embodiments, the transceiver 101 may send analyte data, which may include the analyte concentration, to a display device 105 via the wireless communication protocol. In some embodiments, the transceiver 101 may connect to a personal computer via USB to upload the analyte data history.

In some embodiments, the wireless communication IC 910 may provide a wireless communication interface (e.g., a BLE interface). In some embodiments, the wireless communication IC 910 may be combined with other components (such as an antenna) in a larger package, which may be referred to as a system-in-package (SiP), and may provide a convenient way to treat the entire RF design as a module.

Figure 5:
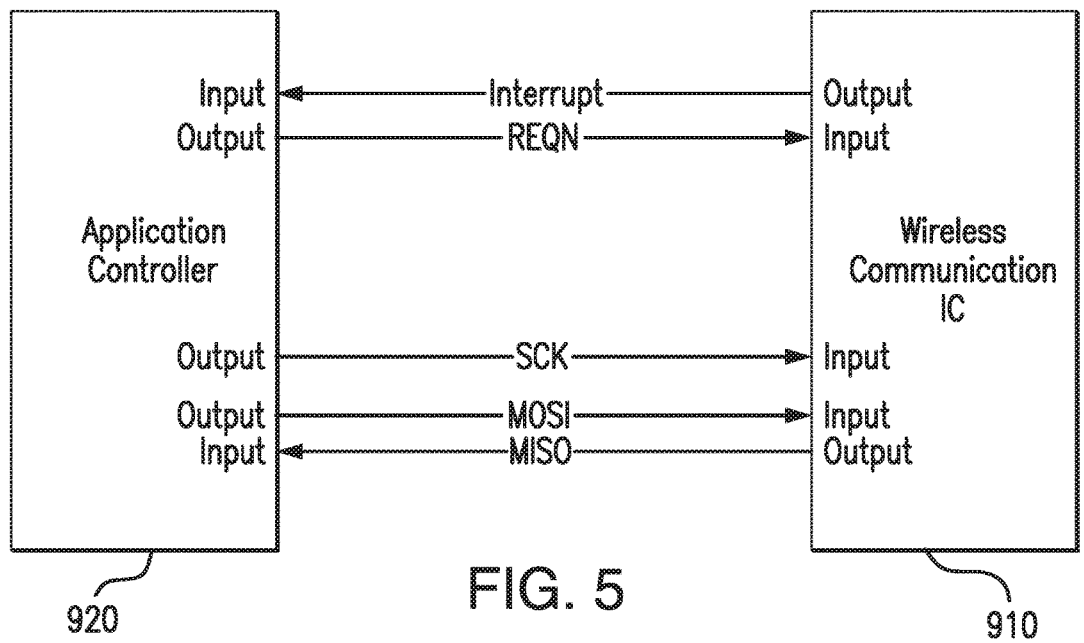
FIG. 5 is a schematic view illustrating connections between an application controller and a wireless communication integrated circuit of a transceiver embodying aspects of the present invention.

FIG. 5 is a schematic view illustrating connections (i.e., the hardware interface) between an application controller 920 and a wireless communication IC 910 of a transceiver 101 embodying aspects of the present invention. In some embodiments, as illustrated in FIG. 5, the application controller 920 and the wireless communication IC 910 may communicate using one or more connections. In some non-limiting embodiments, the connections may include a Serial Peripheral Interface (SPI) connection. In some embodiments, the SPI connection may be a 4-wire serial interface including an SPI clock (SCK) signal output from the application controller 920, a master output-slave input (MOSI) signal from the application controller 920 for communications to the wireless communication IC 910, a master input-slave output (MISO) from the wireless communication IC 910 for communications to the application controller 920, and an SPI chip select (REQN) signal from the output from the application controller 920. In some embodiments, the connections may include one or more additional communications lines, which may include an interrupt (RDYN) signal output from the wireless communication IC 910. In some embodiments, the interrupt line may allow the wireless communication IC 910 to wake up the application controller 920 if the wireless communication IC 910 receives new data over the wireless (e.g., Bluetooth) connection.

In some embodiments, the wireless communication IC 910 may allow for much of the processing related to wireless communications to be offloaded from the application controller 920 on the transceiver 101. In some embodiments, the application controller 920 may send high level commands to perform tasks such as, for example and without limitation, initiating advertising or transmitting data to the wireless communication IC 910. In some embodiments, the wireless communication IC 910 may handle the low level processing of the communications stack.

In some non-limiting embodiments, the software interface between the application controller 920 and the wireless communication IC 910 may be via the Application Controller Interface (ACI). In some embodiments, the ACI may provide a command/response interface via the SPI connection to the wireless communication IC 910. In some embodiments, the application controller 920 may use commands to configure the wireless communication IC 910 and setup communications to a host device (e.g., a communication device 105 such as, for example and without limitation, a display device).

In some non-limiting embodiments, the application controller 920 may use one or more library wrapper functions for one or more of: initializing an ACI library at startup, starting advertising for a connection, starting advertising for a secure (bonded) connection, configuring the wireless communication integrated circuit 910 during startup, resetting the wireless radio (i.e., closing all active connections), initiating a security manager protocol (SMP) security request, reading the security information for storage in non-volatile memory 922, and writing the security information that was stored in memory 922.

In some embodiments, the application controller 920 may be configured to check for data or command responses from the wireless communication IC 910. In some non-limiting embodiments, the interrupt signal from the wireless communication IC 910 may indicate that there is new data for the application controller 920 (e.g., the interrupt signal may be pulled low when there is new data). In some embodiments, the application controller 920 may be configured such that the indication from the interrupt signal will generate an interrupt and wake the application controller 920 from a sleep mode. In some non-limiting embodiments, the application controller 920 may then process the ACI event data using the library wrapper functions.

In some non-limiting embodiments, the wrapper functions may call an appropriate callback (hook) function for the event that occurred. In some non-limiting embodiments, the ACI library callbacks (hooks) may be utilized in by the application controller 920 to determine one or more of: whether the wireless communication IC 910 is initialized and ready to be configured, whether the wireless communication IC 910 is configured and ready, whether an advertising session has expired, whether the wireless connection (e.g., BLE connection) to the display device 105 (e.g., mobile handheld device) has ended, whether connection to a display device 105 has been established, whether a bonding status update has occurred, and whether a response from a command has been received, whether service data has been received.

In some embodiments, the wireless communication IC 910 software development kit (SDK) may include a tool for configuring the communication channels between the application controller 920 and the wireless communication IC 910. In some non-limiting embodiments, the output of this tool may be a set of automatically generated files. In some embodiments, the application controller 920 may utilize a function call to send application data to the host device (e.g., a communication device 105 such as, for example and without limitation, a display device).

In some embodiments, the wireless protocol may provide an interface abstraction known as a service. A service is a set of data items (characteristics) and its associated behavior. In some embodiments, the wireless protocol may include a number of predefined services that can be used by applications. In some embodiments, the services are combined together in embodiments known as profiles for applications. In some embodiments, custom services and profiles are possible for the wireless protocol. For example, custom services and profiles are possible with the BLE protocol. In some embodiments, the transceiver 101 may use a custom service. In some non-limiting embodiments, the custom service may include one characteristic for transmitting and another characteristic for receiving data. In some non-limiting embodiments, the service itself and each characteristic in the service may contain a universally unique identifier (UUID).

In some embodiments, the characteristics of the custom service of the transceiver 101 may essentially be data streams for transmitting and receiving blocks of data. In some non-limiting embodiments, the blocks of data may be 20 byte blocks of data. However, this is not required and other sizes may be used for the blocks of data. In some embodiments, the application controller 920 of the transceiver 101 may use the general purpose data streams to communicate one or more of commands, responses, and "push" type data with a remote display device 105 (e.g., a handheld mobile device or smartphone).

In some embodiments, the wireless protocol provides the capability of specifying responses to data that is transmitted via characteristics. For example, the BLE protocol provides the capability of specifying responses to data that is transmitted via characteristics. In some embodiments, the responses may be generated automatically or manually.

In some embodiments, data that is transmitted via the wireless communication protocol may be encapsulated in packets during communication. In some non-limiting embodiments, data transmitted via the wireless communication protocol may be encapsulated in one or more packet formats. In some non-limiting embodiments, the packet formats may include one or more of a first, second, and third packet format.

In some embodiments, the first packet format may be used for communication between the application controller 920 and the wireless communication IC 910, which may be via an SPI interface. The first packet format may be, for example and without limitation, an ACI packet format. In some embodiments, the first packet format may include, for example and without limitation, a byte that specifies the length of the payload, a byte that specifies an opcode, and a payload of up to 30 bytes.

In some embodiments, the application controller 920 may generate application data, which may comprise one or more analyte concentrations, and encapsulate the application data in one or more packets for the first format. In some embodiments, the wireless communication IC 910 may receive the application data in the one or more packets of the first format from the application controller 920. Similarly, in some embodiments, the wireless communication IC 910 may encapsulate data received from a display device 105 in one or more packets of the first format, which may then be received by the application controller 920.

In some embodiments, the second packet format may be used for link layer communication between the wireless communication IC 910 and a display device 105. For example, in embodiments where the wireless communication protocol is the BLE protocol, the link layer communication may include one or more of <Preamble>, <Header>, and <Payload>. The second packet format may be, for example and without limitation, a BLE packet format. In some embodiments, the second packet format may include, for example and without limitation, a byte for a preamble, four bytes for an address, one byte for a header, one byte that specifies the length of the payload, a variable length payload, and two or three bytes for an error detection code such as, for example and without limitation, a cyclic redundancy check (CRC). In some embodiments, the link layer may be the most complex and robust communication layer utilized. For example, in embodiments where the wireless communication protocol is the BLE protocol, the link layer may include features such as sequence numbering, frequency hopping, encryption, and integrity checking via a 24 bit CRC. In some embodiments, these features may allow for the removal of the sync and length bytes from the standard application layer protocol (as used by the USB interface). Further details of the BLE link layer can be found in the Core Bluetooth Specification v4.0.

In some embodiments, the third packet format may be used for application layer messages between the wireless communication IC 910 and a display device 105. In some embodiments, the second packet format may include, for example and without limitation, one byte that specifies a command (i.e., a command ID), a payload of up to maximum number of bytes, and two bytes for an error detection code such as, for example and without limitation, a CRC. In some embodiments, the wireless communication protocol may limit the length of a communication packet and may, therefore, limit the maximum length of the third packet format payload. For example, the BLE protocol limits the length of a communication packet to a maximum of 25 octets and, therefore, may limit the third packet format payload to a maximum of 22 octets (e.g., due to the overhead of a one byte command ID and a two byte CRC). In some embodiments, the wireless communication IC 910 may limit the length of a communication packet and may, therefore, limit the length of the third packet format payload. For example, in some non-limiting embodiments, the wireless communication IC 910 may limit the length of a communication packet to a maximum of, for example and without limitation, 20 octets. As a result, in some embodiments where communication packets are limited to 20 octets, the third packet format payload may be limited to a maximum of 17 octets (e.g., due to the overhead of a one byte command ID and a two byte CRC).

In some embodiments, the wireless communication IC 910 may receive application data from the application controller 920 and encapsulate the application data in one or more packets of the third format. In some embodiments, a display device 105 may receive the application data in the one or more packets of the third format from the wireless communication IC 910. In some embodiments, the application data may comprise one or more analyte concentrations calculated by the application controller 920.

Figure 6:
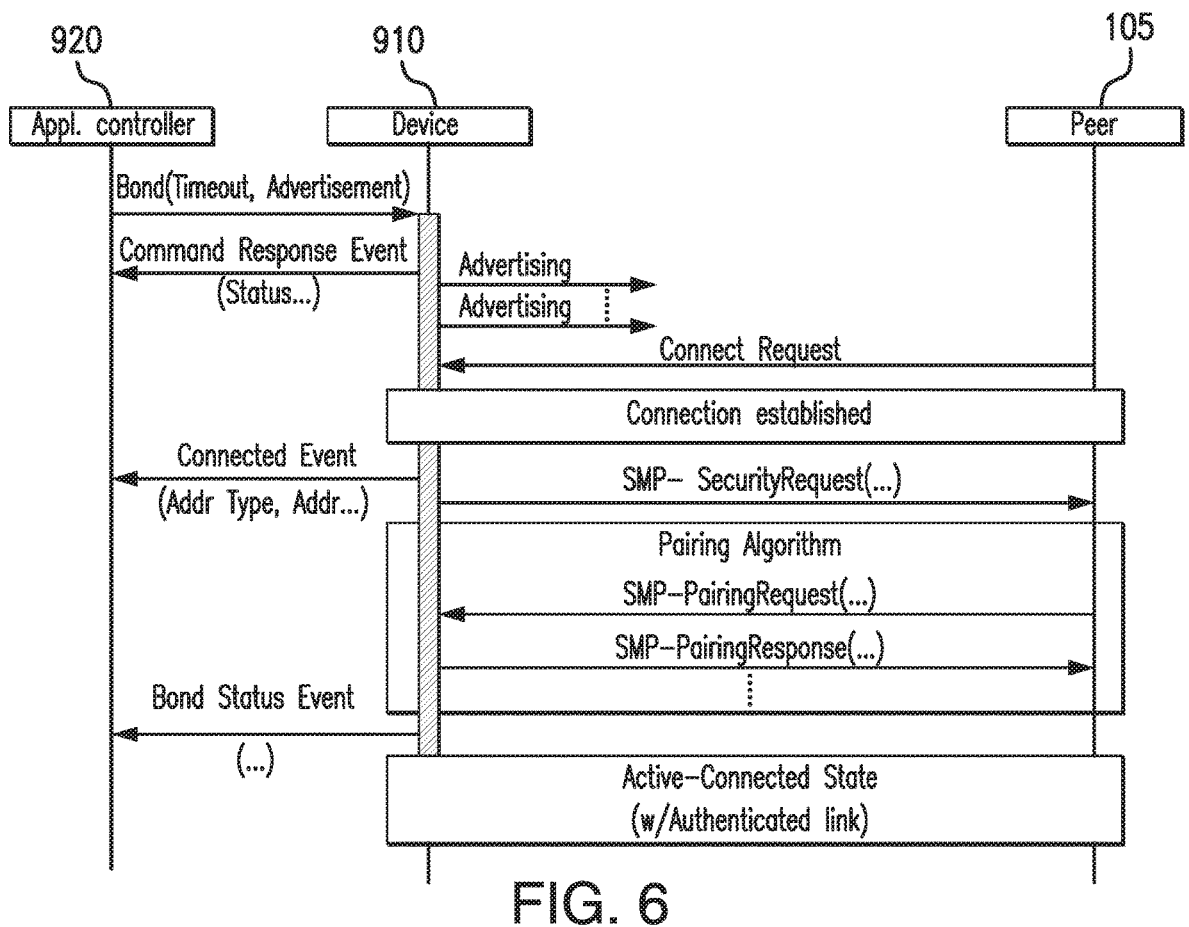
FIG. 6 is a sequence diagram illustrating the system level connection process for creating a secure connection embodying aspects of the present invention.

In some embodiments, the transceiver 101 may use a custom that has security enabled. In these embodiments, communication using the transmit and receive characteristics may not be possible unless a secure connection (i.e., bond) is made between the transceiver 101 and the remote display device 105. In some non-limiting embodiments, the application controller 920 of the transceiver 101 may enable security by calling an ACI library wrapper function starting advertising for a secure (bonded) connection. In some embodiments, this command will start a limited mode advertisement for up to a period of time (e.g., 30 seconds). In some embodiments, when the display device 105 connects, the application controller 920 of the transceiver 101 may send the library wrapper function command for initiating an SMP request to initiate the bonding procedure. FIG. 6 is a sequence diagram illustrating the system level connection process for creating a secure connection according to some non-limiting embodiments. In some embodiments, after a bond has been established between the transceiver 101 and the display device 105, communication via the custom service is enabled. In some embodiments, subsequent communication may be encrypted with one or more security keys, which may be stored on the wireless communication IC 910. In some non-limiting embodiments, the security information may additionally or alternatively be stored to non-volatile memory 922 on the transceiver 101 (e.g., using the library calls for reading and writing the security information for storage in the non-volatile memory 922). In some embodiments, storing the security information in the non-volatile memory 922 may allow for the security information be retained even after power is lost to the transceiver 101.

In some embodiments, there may be one or more modes of advertising utilized by the transceiver application. In some embodiments, the transceiver 101 may include an advertising mode in which the transmitter 101 advertises for a secure (bonded) connection. In some embodiments, this advertising mode may be initiated using a library function that starts the advertising for the secure connection. In some embodiments, the transceiver 101 may additionally include a non-discoverable advertising mode in which the transceiver 101 has previously bonded to a display device 105 and is advertising to connect again. In some embodiments, the non-discoverable advertising mode may be initiated using a library function that starts advertising for a connection. In some embodiments, the non-discoverable advertising mode can remain active for a variable amount of time (typically infinite).

In some embodiments, in both the advertising mode for the secure connection and the non-discoverable advertising mode, the transceiver 101 may transmit advertising packets (e.g., ADV_IND packets) which are visible to all scanners. In some embodiments, the distinction between the advertising modes may be that the non-discoverable advertising mode permits the use of existing security keys once a connection is established. In some embodiments, in the non-discoverable advertising mode, if a different display device 105, which does not have matching security keys, attempts to connect to the transceiver 101, then the connection attempt will fail.

In some embodiments, the advertisement message may be configurable and may contain (1) the name of the transceiver 101 and/or (2) a custom service UUID. In some embodiments, the name of the transceiver 101 may be written in a communication device name field, which may be, for example and without limitation, up to 8 characters. In some embodiments, in order for bonding information to be saved, a radio reset must be performed. In some embodiments, the display device 105 can trigger a radio reset.

In some embodiments, the display device 105 may act as the connection initiator. In some embodiments, the display device 105, as the connection initiator, may specify a desired initial connection interval in its connection request packet. In some embodiments, the transceiver 101 may be able to request a change to the connection interval. In some embodiments, the transceiver 101 may use, for example and without limitation, an L2CAP Connection Parameter Update request to request the change to the connection interval. In some embodiments, the transceiver 101 may act as a peripheral. In some embodiments, the transceiver 101 may initiate a request to change the connection interval by calling a library function. In some embodiments, the transceiver 101 may request a reduction in the connection interval. In some non-limiting embodiments, the transceiver 101 may request a connection interval that is the minimum connection interval permitted by the display device 105. For example, in a non-limiting embodiment where the display device 105 is an iOS device that permits a minimum connection interval of 18.75 ms, the transceiver 101 may request a connection interval of 18.75 ms. In some non-limiting embodiments, a connection interval of 18.75 ms may be obtained using a minimum connection interval parameter of 0x10 and a maximum connection interval parameter of 0x20. In some embodiments, outside of a short period at the start of each connection interval (CI), both the transceiver 101, which may act as a peripheral, and the display device 105, which may act as a central, can power down the wireless (e.g., BLE) radio.

In some embodiments, the wireless communication IC 910 may be capable of sending two or more data packets during each connection interval. In some embodiments, the wireless communication IC 910 may be capable of sending two or more data packets during each connection interval by not waiting for a response from the display device 105 that a first of the two or more packets was received. In some embodiments, each of the two or more data packets may be transferred at the start of the connection interval. In some embodiments, the wireless communication IC 910 may send the two or more data packets to the display device 105 as write without response messages. In some embodiments, the wireless communication IC 910 may send two or more data packets during one or more of the connection intervals. In some embodiments, the number of data packets transferred during a collection interval may be indicated by the number of Data Credits indicated in a callback triggered by the DeviceStartedEvent on the wireless communication IC 910.

In some embodiments, the wireless communication IC 910 may receive all of the packets from the application controller 920 by the start of a connection interval in order for wireless communication IC 910 to be able to send the two or more data packets during the connection interval. In some embodiments, the transmitter 101 may include a transmit queue. In some embodiments, the transmit queue may be an internal component of the wireless communication IC 910. However, this is not required, and, in some alternative embodiments, the transmit queue may be external to the wireless communication IC 910. In some embodiments, the transmit queue may help to ensure that, when sending responses from the transceiver 101, all available data credits are used. In some embodiments, the transmit queue may queue data to be sent to the display device 105, and the queued data may be dequeued as soon as a credit becomes available. In some embodiments, the transceiver 101 may use a new range of multi-response packet responses for log-reading to help ensure that, when sending responses from the transceiver 101, all available data credits are used.

In some embodiments where the wireless communication IC 910 limits the maximum data packet payload to 20 bytes, the application level payload may be limited to, for example and without limitation, 17 bytes due to an application level overhead of a one byte command ID and a two byte CRC. In these embodiments, the maximum achievable data transfer rate from the transceiver 101 to a display device 105 that limits the minimum connection interval to a minimum of 18.75 ms is 106 packets/second, which is equal to (2 packets per connection interval)/(18.75 ms per connection interval). At 17 usable bytes per application level message, this corresponds to a nominal transfer rate of 1.8 kbyte/sec, independently in each direction.

Figure 7:
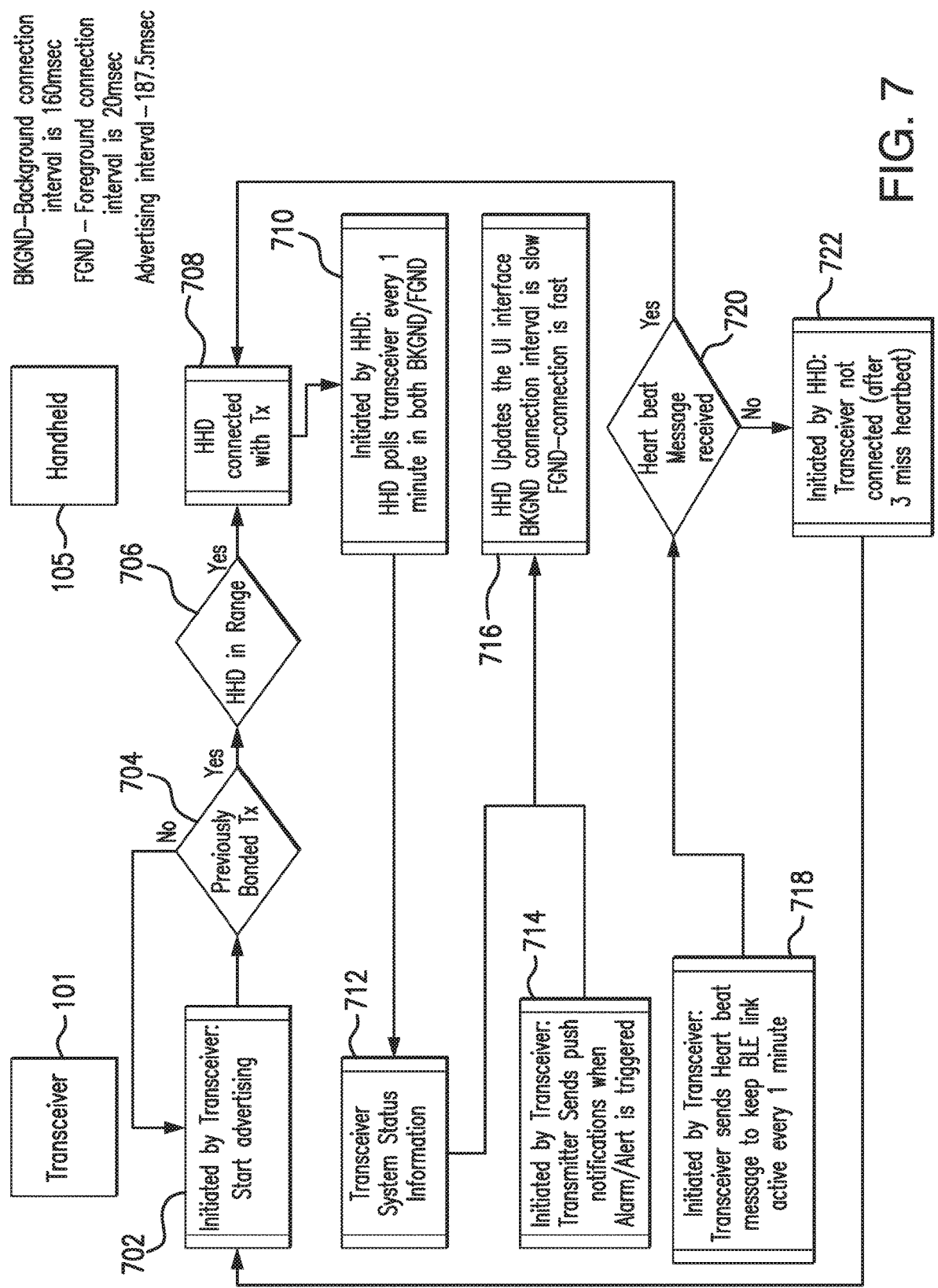
FIG. 7 is a flowchart illustrating a non-limiting example of a process for wireless communication between first and second communication devices embodying aspects of the present invention.

FIG. 7 is a flowchart illustrating a non-limiting example of a process 700 for wireless communication between first and second communication devices, which may be, for example and without limitation, the transceiver 101 and the display device 105, respectively. In the flowchart, steps of process 700 that may be performed by the transceiver 101 are shown on the left, and steps of process 700 that may be performed by the display device 105 are shown on the right.

In some embodiments, the process 700 may include a step 702 in which the transceiver 101 starts advertising for a connection. In some embodiments, the process 700 may include a step 704 that determines whether the transceiver 101 has bonded previously with a display device 105 and has security information (e.g., keys) for a secure connection with the display device 105. In some embodiments, the process 700 may include a step 706 that determines whether a display device 105 is within range. In some embodiments, the process 700 may include a step 708 that creates a secure connection between the transceiver 101 and a display device 105 if the display device 105 is within range and the transceiver 101 has security information for the display device 105.

In some embodiments, the process 700 may include a step 710 in which the connected display device 105 polls the transceiver 101. In some non-limiting embodiments, the display device 105 may poll the transceiver 101 for one or more of analyte information, transceiver battery information, and overall system information. In some non-limiting embodiments, the display device 105 may poll the transceiver 101 periodically. For example and without limitation, the display device 105 may poll the transceiver 101 every one 1 minute. However, this is not required, and, in some alternative embodiments, the display device 105 may poll the transceiver 101 at different frequencies (e.g., every 30 seconds or every 2 minutes).

In some embodiments, the display device 105 may execute a mobile medical application (MMA). In some embodiments, the MMA may run on the display device 105 in the foreground or in the background. In some embodiments, the display device 105 may execute a mobile medical application (MMA). In some embodiments, the MMA may run on the display device 105 in the foreground or in the background. In some embodiments, the display device 105 may the transceiver 101 regardless of whether the MMA is in the foreground or the background. In some non-limiting embodiments, the display device 105 may poll the transceiver 101 at the same frequency (e.g., every one 1 minute) regardless of whether the MMA is in the foreground or the background. However, this is not required, and, in some alternative embodiments, the display device 105 may poll the transceiver 101 at one frequency when the MMA is in the foreground and at a different frequency when the MMA is in the background.

In some embodiments, the process 700 may include a step 712 in which the transceiver 101, in response to a polling from the display device 105, sends data to the display device 105. In some embodiments, the data sent to the display device 105 may include system status information. In some non-limiting embodiments, the system status information may include one or more of analyte concentration information, calibration reminders, active alert information, transceiver batter information, information about communication between the sensor 100 and transceiver 101.

In some embodiments, the process 700 may include a step 714 in which the transceiver 101 sends one or more push notifications to the display device 105. In some embodiments, the transceiver 101 may sends the one or more push notifications to the display device 105 when the transceiver 101 detects an alert or alarm condition. In some embodiments, the alert or alarm conditions detected by the transceiver 101 may include, for example and without limitation, one or more of high analyte concentration, low analyte concentration, predicted high analyte concentration, predicted low analyte concentration, analyte concentration calculation calibration needed, low transceiver battery, sensor replacement needed, predicted sensor replacement, and loss of sensor communication. In some embodiments, the one or more push notifications may include an indication of the alert or alarm condition that was detected by the transceiver 101.

In some embodiments, the process 700 may include a step 716 in which the display device 105 updates the user interface on the display device 105 based on one or more of the data received in step 712 (e.g., system status information such as, for example and without limitation, analyte concentration information) and the push notification(s) received in step 714. In some embodiments, the MMA executed on the display device 105 continues to be updated regardless of whether the MMA is running in the foreground or in the background.

In some embodiments, the transceiver 101 may send data (e.g., application data) to the display device 105 at a relatively fast rate when the MMA executed by the display device 105 is in the foreground and at a relatively slow rate when the MMA is in the background. In some embodiments, the MMA executed by the display device 105 may inform the transceiver 101 that the MMA is going from the foreground to the background. In some embodiments, the transceiver 101 may, in response to receiving an indication that the MMA is going to the background, decrease the data rate by requesting an increased connection interval. For example and without limitation, the transceiver 101 may request a background connection interval of 160 ms. In some embodiments, the MMA may inform the transceiver 101 that the MMA is going from the background to the foreground. In some embodiments, the transceiver 101 may, in response to receiving an indication that the MMA is going to the foreground, increase the data rate by requesting a decrease to the connection interval. For example and without limitation, the transceiver 101 may request a foreground connection interval of 20 ms.

In some embodiments, the process 700 may include a step 718 in which the transceiver 101 sends a heartbeat message to the display device 105 to keep the wireless connection (e.g., the BLE connection) between the transceiver 101 and the display device 105 active. In some non-limiting embodiments, the heartbeat message may include date/time information. In some non-limiting embodiments, the heartbeat message may include no payload. In some embodiments, the heartbeat message from the transceiver 101 may indicate to the display device 105 that the transceiver 101 is still connected over the wireless connection. In some embodiments, transceiver 101 may send the heartbeat message to the display device 105 periodically. For example and without limitation, the display device 105 may send a heartbeat message to the display device 105 every minute. However, this is not required, and, in some alternative embodiments, a different time interval may be used.

In some embodiments, the process 700 may include a step 720 in which the display device 105 determines whether a heartbeat message has been received from the transceiver 101. In some embodiments, the process 700 may proceed to step 708 if a heartbeat message has been received. In some embodiments, the display device 105 may determine whether a threshold number of expected heartbeat messages were not received. In some non-limiting embodiments, the threshold number of missed heartbeat messages may be, for example and without limitation, three. In some alternative embodiments, the display device 105 may determine whether a threshold period of time has passed without receipt of a heartbeat message from the transceiver 101. In some non-limiting embodiments, the threshold period of time may be, for example and without limitation, 3 minutes.

In some embodiments, the process 700 may include a step 722 in which the display device 105 terminates the connection with the transceiver 101. In some embodiments, the process 700 may proceed to a step 722 if step 720 determines that three consecutive heartbeat messages were missed or that the threshold period of time has passed without receipt of a heartbeat message. In some embodiments, the display device 105 may terminate the connection with the transceiver 101 if it appears that the transceiver 101 is no longer connected to save resources. In some embodiments, the display device 105 may inform a user that the connection with the transceiver 101 was disconnected. In some embodiments, after a connection is lost, the transceiver 101 may advertise to re-establish the connection (e.g., step 702).

In some embodiments, the heartbeat message processing (e.g., steps 718, 720, and 722) may keep the transceiver 101 and the display device 105 connected so that the transceiver 101 is able to send one or more push notifications to the display device 105 (e.g., in step 716) at any time. For example, in embodiments where the communication system 50 is an analyte monitoring system, the alerts and alarms from the transceiver 101 may relate to a time-sensitive, emergency medical condition (e.g., hypo- or hyper-glycemia), and a user of the communication system 50 may want to receive alerts and alarms from the transceiver 101 via the display device 105 without delay and without missing any alerts or alarms.

In some alternative embodiments, in step 720, instead of looking solely for receipt of a heartbeat message, the display device 105 may determine whether any message (e.g., heartbeat message, system status information, or push notification) has been received from the transceiver 101 to determine whether the transceiver 101 is connected. In some alternative embodiments, the process 700 may not include a step 718 in which the transceiver 101 sends a separate heartbeat message to keep the wireless connection between the transceiver 101 and the display device 105 active, and, in step 720, the display device 105 may determine whether the connection is active based on whether system status information or a push notification has been recently received by the display device 105 from the transceiver 101.

In some embodiments, the display device 105 is the master, and the transceiver 101 is the slave. However, this is not required. In some alternative embodiments, the transceiver 101 may be the master if the display device 105 goes out of range, and the transceiver 101 may look for a different display device to pair with. Also, in some alternative embodiments (e.g., closed-loop embodiments in which an insulin pump is integrated into the communication system 50 with the sensor 100 and transceiver 101), the transceiver 101 may be the master.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention.

What is claimed is:

1. A first communication device for communicating wirelessly with a second communication device during connection intervals having a length agreed upon by the first and second communication devices, the first communication device comprising:
   an application controller configured to generate application data;
   an antenna; and
   a wireless communication integrated circuit (IC) configured to (i) receive the application data from the application controller, (ii) encapsulate the application data in data packets, (iii) use the antenna to transmit one or more of the data packets to the second communication device during each of one or more of the connection intervals, and (iv) in response to using the antenna to receive from the second communication device an indication that an application being executed by the second communication device is going to the background, use the antenna to transmit to the second communication device a request for an increased connection interval to decrease the data rate, and (v) in response to using the antenna to receive from the second communication device an indication that the application is going to the foreground, use the antenna to transmit a request for a decreased connection interval to increase the data rate.

2. The first communication device of claim 1, wherein the wireless communication IC is configured to use the antenna to transmit the one or more data packets to the second communication device during each of the one or more connection intervals without waiting for a response that a first of the one or more data packets was received.

3. The first communication device of claim 1, wherein the wireless communication IC is further configured to use the antenna to transmit a request for a change to the length of the connection intervals to the second communication device.

4. The first communication device of claim 1, wherein the application controller is further configured to receive one or more raw signals from an analyte sensor and use the one or more raw signals to calculate one or more analyte concentrations, wherein the application data comprises the one or more analyte concentrations.

5. The first communication device of claim 4, wherein the one or more raw signals include one or one or more analyte measurements and one or more temperature measurements.

6. The first communication device of claim 1, wherein the wireless communication IC is further configured to, during periods when there is no application data for the wireless communication IC to encapsulate and transmit to the second communication device, use the antenna to transmit a message to the second communication device, and transmitting the message keeps the wireless link between the first and second communication devices active.

7. The first communication device of claim 1, wherein the wireless communication IC is further configured to use the antenna to transmit to the second communication device a request that the length of the connection intervals be the minimum connection interval permitted by the second communication device.

8. The first communication device of claim 1, wherein the length of the connection intervals agreed upon by the first and second communication devices is the minimum connection interval permitted by the second communication device.

9. The first communication device of claim 1, wherein the length of the connection intervals agreed upon by the first and second communication devices is 18.75 ms.

10. The first communication device of claim 1, wherein the wireless communication IC is further configured to power down wireless communication with the second communication device outside of a period at the start of each connection interval.

11. The first communication device of claim 1, wherein the wireless communication IC is configured to use the antenna to transmit the one or more of the data packets to the second communication device during a period at the start of each of one or more of the connection intervals.

12. A method for wireless communication between first and second communication devices during connection intervals having a length agreed upon by the first and second communication devices, the method comprising:
   using the first communication device to generate application data;
   using the first communication device to encapsulate the application data in data packets;
   using an antenna of the first communication device to transmit one or more of the data packets during each of one or more of the connection intervals;
   using the antenna of the first communication device to receive from the second communication device an indication that an application being executed by the second communication is going to the background;
   in response to receiving the indication that the application being executed by the second communication device is going to the background, using the antenna of the first communication device to transmit to the second communication device a request for an increased connection interval to decrease the data rate;
   using the antenna of the first communication device to receive from the second communication device an indication that the application being executed by the second communication is going to the foreground; and
   in response to receiving the indication that the application being executed by the second communication device is going to the foreground, using the antenna of the first communication device to transmit to the second communication device a request for a decreased connection interval to increase the data rate.

13. The method of claim 12, further comprising using the antenna of the first communication device to transmit to the second communication device a request that the length of the connection intervals be the minimum connection interval permitted by the second communication device.

14. The method of claim 12, wherein the length of the connection intervals agreed upon by the first and second communication devices is the minimum connection interval permitted by the second communication device.

15. The method of claim 12, wherein the length of the connection intervals agreed upon by the first and second communication devices is 18.75 ms.

16. The method of claim 12, further comprising powering down wireless communication with the second communication device outside of a period at the start of each connection interval.

17. The method of claim 12, further comprising using the antenna of the first communication device to transmit the one or more of the data packets to the second communication device during a period at the start of each of one or more of the connection intervals.

* * * * *